United States Patent [19]
Nauert

[11] Patent Number: 6,066,110
[45] Date of Patent: May 23, 2000

[54] USER CUSTOMIZABLE KNEE BRACE

[76] Inventor: Richard S. Nauert, 351 N. Newport Blvd., No. 120 Newport Beach, Calif. 92663

[21] Appl. No.: 09/177,877

[22] Filed: Oct. 23, 1998

[51] Int. Cl.[7] .................................................... A61F 5/00
[52] U.S. Cl. .............................................. 602/26; 602/16
[58] Field of Search ................................ 602/26, 62, 23, 602/16

[56] References Cited

U.S. PATENT DOCUMENTS

| | | | |
|---|---|---|---|
| 4,986,264 | 1/1991 | Miller | 128/80 |
| 5,288,287 | 2/1994 | Castillo et al. | 602/16 |
| 5,693,007 | 12/1997 | Townsend | 602/26 |
| 5,743,865 | 4/1998 | Townsend | 602/26 |
| 5,782,780 | 7/1998 | Mason et al. | 602/26 |

*Primary Examiner*—Richard J. Apley
*Assistant Examiner*—Jayne Saydah
*Attorney, Agent, or Firm*—Curtis L. Harrington

[57] ABSTRACT

An extended coverage leg brace having an up and across upper and down and across lower structure carries a number of extended adjustment areas. The structure provides an extended length moment engagement to reduce pressure on the upper and lower leg of the user, while the adjustment areas facilitate and enable the user to form the brace to a configuration which will better fit the user's leg shape and topology. The shape of the upper and lower supports in addition to smaller adjustment area loops produces a large open space which avoids over covering the skin of the upper and lower leg to promote air and cooling to significant areas of the upper and lower leg. A custom pad set has raised areas which fit somewhat through the open spaces left in the looping upper and looping lower structural supports which enable the use of lighter weight and a lesser amount of more efficient padding, which also promotes "breathing" adjacent the leg.

20 Claims, 5 Drawing Sheets

USER CUSTOMIZABLE KNEE BRACE

FIELD OF THE INVENTION

The present invention relates to an improved, off-the-shelf orthopedic device for the stabilization and control of a human knee joint of the left and or the right leg and having an extended coverage but reduced area and lighter weight structure and which can be custom formed in various zones by the user or technician to closely fit to the upper and lower portions of the leg of a wearer to optimize comfort, utilization time and protection.

BACKGROUND OF THE INVENTION

The prior art describes many orthopedic devices which attempt to support and stabilize the human knee over a wide range of angular, lateral and rotational displacement of the human leg. In some cases, the device is used by athletes to protect the knee joint. In other instances, an orthopaedic injury or deformity requires a restriction in the flexion and extension or lateral movement of the articulating knee joint to assure that the user will not cause further injury by either extending or flexing beyond a certain angular limit.

Since the leg has significant tissue about the femur, the leg brace has to have significant force coverage, at a greater distance above and below the knee in order to properly stabilize the knee joint. Area coverage relatively closer to the knee joint will otherwise experience a more severe bending moment of the brace against the leg which damages the tissues of the leg. This is known as insufficient leverage. To increase leverage, brace manufacturers have lengthened the cuffs. As length increases, so to does the possibility of a mismatch, or gap, between the brace and the leg's surface. These gaps are typically filled by adding padding or by heating and re-shaping the frame of the brace.

Another problem with braces are custom formability. A custom brace can be made along with the use of a mold or other physical measurement from the user. This process can be tedious and very costly if it requires participation of technicians, in addition to the user. A precise fit was only achieved by making the brace by hand on a model of the patient's leg, or by reheating a re-shapable plastic shell or by adding more and more padding materials to fill voids in the brace shape to compensate for the mismatch between the brace support and the leg. Heating a brace to re-form it requires an additional step in the fitting process. Where a patient's or user's leg musculature changes from increased or decreased athletic activity or weight gain or loss, the brace must be brought in for the technician to re-heat and re-fit. This time consuming process requires additional expertise and equipment to perform correctly and efficiently.

The addition of padding to try to achieve a custom fit from an off-the-shelf brace was even more of a disaster since more padding needs to be utilized. Padding creates a further deviation from a good fit. The padding can be compressed during utilization of the brace, and the compression "loosens" the effective fit of the brace. Even more importantly, the padding does not help maintain the most minimal profile possible and there will always be unnecessary bulk in the padded areas.

In some cases, a close covering fit based upon a mold can be as confining as conventional cuff or an extended solid support. Where solid coverage is used, especially with a reinforcement to make them lighter weight, they are not shapable. Also, custom braces are not user adjustable, in addition to being overly expensive to make.

Conventional braces are not customizable beyond a tightening or loosening of the straps holding them in place, and the adding or taking away of padding, or the application of heat to soften the frame for adjustment. This is unfortunate, since the topology of the leg, knee and calf offers ample opportunity for some customizable fit to take advantage of the user's shape and contour.

Even where the confinement problem is not present, a custom formed brace can't easily or instantly be adjusted instantly for changes in the size of the leg, such as occurs during an injury and long periods of inactivity, or such as might occur as the leg muscles are bulked up with increased athletic activity or injury, or when leg muscles reduce in size due to atrophy, or from normal human weight gain or loss.

Another problem with conventional braces is the bulky fittings which may be present to enable engagement of the straps. D ring strap fittings usually depend from fittings which are attached to the cuff through rivets or other fastening structures. Whenever the cuff structures have such extraneous additional structure for fitting the straps, user discomfort is increased from added bulk, and a low profile is impossible to achieve. Such discomfort is answered with more and thicker padding, which further reduces fit and performance.

Another problem with braces used during athletic activity is the tendency of the brace to ride down on the leg when the athlete runs. When this problem is approached by tightening the straps, discomfort and restriction of circulation occurs. Even partial downward shifting of the brace interferes with the proper operation of the brace.

Another problem with conventional braces is the lack of even compression of the soft tissues of the leg against the internal structure of the bones whose position and movement are to be controlled. As force is applied to a conventional brace, uneven support of the leg is the result. This is particularly the case with a conventional brace which uses full circumference straps since such straps follow the contour of the leg and only contain the volume of the leg at the point at which the strap is located. This does not necessarily maintain original shape as a load is applied. This distortion of the shape can allow the bones to misalign sufficiently to damage the ligaments about the knee. For some designs, a misalignment problem can be worsened by the improper addition of pads to create an appearance and feel of an accurate fit in an unloaded state, but which may compress and allow misalignment and damage under load if the overall design of the conventional brace does not allow for it.

What is therefore needed is a light weight brace, having an extended length moment or leverage engagement with the leg, but without providing more skin coverage than necessary, allows for exchange of air or "breathing" to take place within the brace, and importantly enables customization adjustments to be easily performed. The customization adjustments should both take advantage of the topography of the user's leg, as well as to enable adjustment as the size of the leg changes, either because of increase or decrease in the size of the leg.

SUMMARY OF THE INVENTION

The brace of the present invention can be custom formed by the user or technician to closely fit to the upper and lower portions of the leg of a wearer to optimize factors including comfort, utilization time and protection and promote healing. These factors are individually and collectively optimized by a more perfect fit between the structural brace and the surface of the leg.

The inventive knee brace has a number of adjustable "contour zones" to quickly permit adjustment of the brace over the widely varying ranges in shape of the human leg, and without heat. This new design allows a quick optimal fit and maintains a very low profile.

The design allows the brace the maximum leverage and control by a more exacting fit close to the knee joint, as well as at the uppermost and lowermost edges of the brace. The inventive brace has "contour zones" directly above the knee and below the knee in the form of adjustment members which wrap the leg inwardly from the sidebars of the upper support to a point almost to the center line of the leg and are bendable toward or away from the surface of the leg, the bending to achieve a shape which will withstand normal use. Since the contour zone adjustment members on the upper part of the brace are somewhat elongated shape, the ability to control not only the degree of bending toward and away from the leg, but also variations in the radius and contour of the adjustment member is possible.

The material making up the "adjustment zones", along with the varying sizes of widths between the hinges and uprights along the sides of the user's leg allow for the closest support by a solid lightweight metal framework. The brace framework circumferentially contacts the leg as close to the knee joint as is practically possible without interfering with the joint's movement. After proper sizing and adjustment, this framework structure closely contacts the sides as well as the front of the shin and thigh close to the joint without interfering with the knee cap area or the popetiel (behind the knee) area.

At upper and lower ends of the brace, four "mold zones" are located at each of the inner and outer corners to adjust for the varying contours of the leg's surface as well as the general overall varus or valgus (knock-kneed or bow-legged) condition of the user. This allows the brace to follow the angle of the user's upper leg relative to the lower leg and to conform easily thereto, so as to avoid an area over the length if the brace where a mismatch would cause a corner to "stick out" from or to "dig into" or gouge the user's leg.

The framework has a unique design which, along with its associated strapping, allows each of the upper and lower leg engagement portions to fit exactly over the entire surface of the upper and lower parts of the user's leg. This close fitting feature minimizes the tendency for the soft tissue to distort by effectively containing and then compressing soft tissues in their original unloaded shape.

Where the brace has angular front to back displacement with respect to the straight, non-bending portion of the leg, this undesirable effect is known as "rocking" and has several negative consequences. First it requires even more leg coverage for adequate stability. Second, the upper and lower edges of the brace, especially on the upper portion of the leg can gouge into the leg tissue. Third, to overcome rocking requires a tighter fit thus placing greater restriction on the leg tissues and increasing discomfort.

The close fit over the length of each of the upper and lower leg engaging "shells" also keeps the adjacent bone from "rocking". This can be best understood by picturing a knee brace with a single narrow band crossing the tibia and femur at a distances of about eight inches below and eight inches above the knee. If a rearward force was applied at the knee and the user was putting weight on the leg, there would be a tendency for the bones to pivot or rock on the framework of the brace, which includes the danger of hyper extending the knee joint. Conversely, if it were possible to support the tibia with a wide band across the bones and close the joint and of sufficient length of about ten inches above the joint and about 10 inches below the knee, the same forces could be applied to a frame having greater leverage, and thus the bones would not "rock" but would remain in a stable, corrective relative position. This type of control is enabled by the brace of the present invention since it has an accurate fit in an area close to the joint and at edges farthest from the joint.

The brace of the invention can have any number of individually identifiable "contour zones" or "mold zones". In fact, the brace has a large number of portions of its material which can be formed, bent or adjusted, and the use of the term "zones" is for illustrative purposes and to identify clusters of bendable areas which are more easily formably bent and shaped.

A custom pad set has raised areas which fit somewhat through the open spaces left in the extended adjustment members and this permits the use of lighter weight and a lesser amount of more efficient padding, which also enables an extremely low profile of the brace on the leg to be achieved. These raised areas also help maintain pad position within the frame.

Additionally, the perfect contour feature of the brace of the invention allows even compression of the soft tissues of the leg against the internal structure of the bones over the length of the brace while position and movement are controlled. As force is applied to the brace of the invention, it tends to keep the leg in its original shape as it compresses the soft tissue evenly. This helps the internal bones of the upper and lower leg to remain in their original positions respective to each other, an important distinction over conventional braces which use full circumference straps since such straps follow the contour of the leg but do not contain the volume of the leg in accord with its original shape as a load is applied. By having an accurate fit of hard shell and minimal padding, the brace of the present invention increases control and leg protection by maintaining shape through even compression of tissues against the bones.

BRIEF DESCRIPTION OF THE DRAWINGS

The invention, its configuration, construction, and operation will be best further described in the following detailed description, taken in conjunction with the accompanying drawings in which.

DETAILED DESCRIPTION OF THE PREFERRED EMBODIMENT

Figure 1:
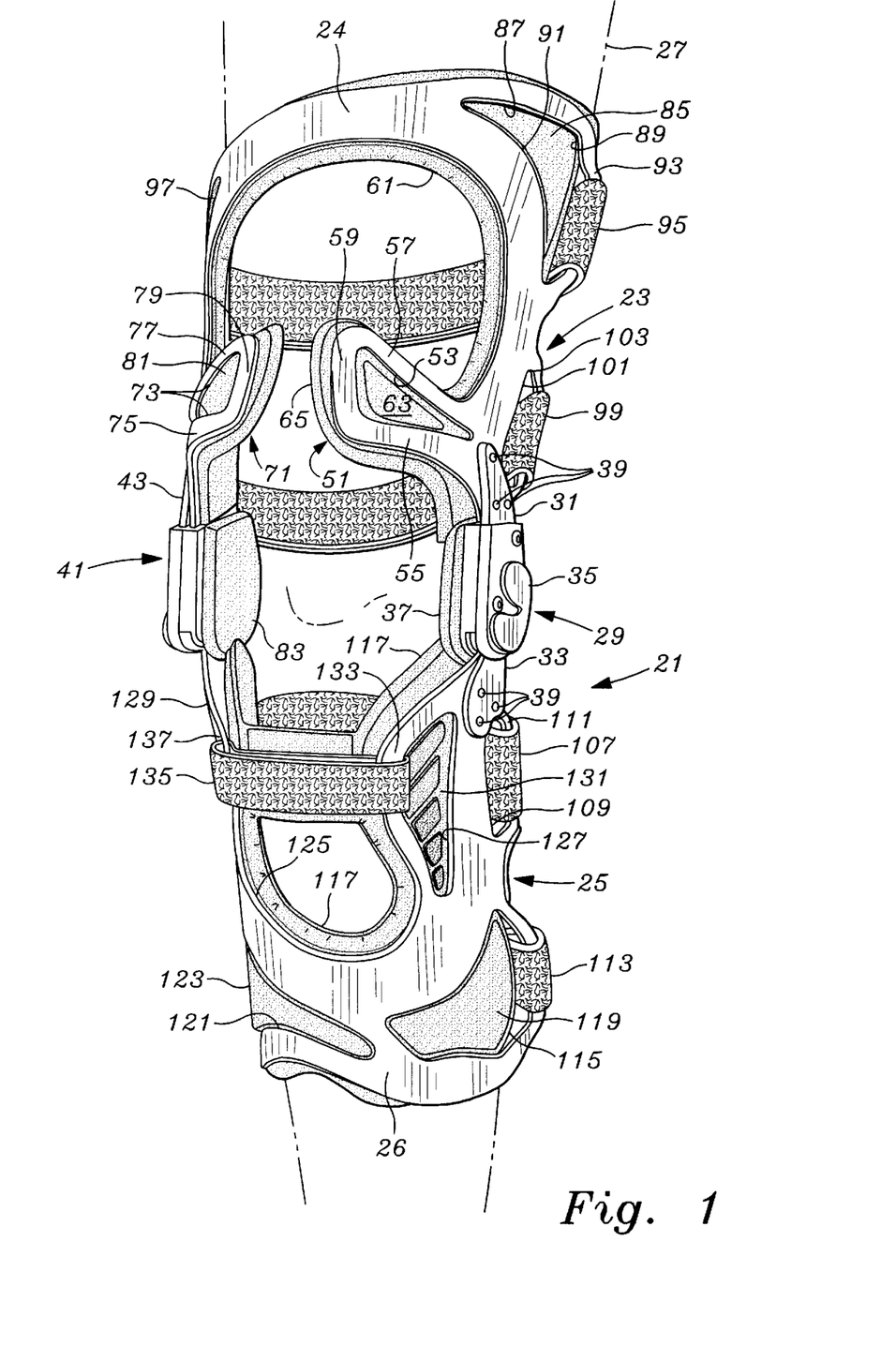
FIG. 1 is a perspective view of the brace of the invention with a left human leg shown in phantom with straps and with a thin layer of padding in place.

A description of the improved brace of the present invention will be best initiated with reference to FIG. 1. A brace 21 has an upper main support 23 having a first vertical side at the right of FIG. 1 and a second vertical side at the left of FIG. 1. Between the vertical sides, the upper main support has a forward curving upper transition member 24 having a top edge. The material seen in the main structural expanse of brace 21 is preferably coated in a plastic material as by dipping or spraying. Brace 21 has a lower main support 25 also having a first vertical side at the right of FIG. 1 and a second vertical side at the left of FIG. 1. Between the vertical sides of lower main support 25, a forward transition member 26 is seen and has a bottom edge. The brace 21 is shown around a human leg 27, shown in dashed line format. A hinge 29, located near a first lower end of upper main support 23 and a first upper end of lower main support 25, may include an upper metal plate 31 and a lower metal plate 33 to facilitate attachment of the hinge 29 to the upper main support 23 and a lower main support 25, especially where a strong hinge 29 is required. As will be seen, the use of an integral hinge which joins downwardly extending portions of upper main support 23 and upwardly extending portions of lower main support 25 are also possible.

A polymeric cover 35 secures and protects the inner working portion of the hinge 29. An inner polymeric cover 37 opposes the leg 27 and may be further covered with a softer member by adhesive or hook and loop member attachment. A series of screws 39 attach the hinge 29 to the upper main support 23 and a lower main support 25 through upper metal plate 31 and a lower metal plate 33. The use of rivets or welding or gluing are equally possible variations to attach hinge 29.

The upper main support 23 extends generally upward from the area where it connects Lo the upper metal plate 31, and then forward across the top of the leg 27 and to the other side of leg 27 and downward to a hinge 41, located adjacent a second lower end of the upper main support 23 and a second upper end of the lower main support 25. Hinge 41 also has an upper metal plate 43, and a lower metal plate (indicated but not directly seen in FIG. 1) which is a mirror image of lower metal plate 33.

Immediately above and adjacent the upper metal plate 31, the upper main support has a first extended member 51 which extends in a direction across the leg 27, but does not extend past the midpoint of the brace 21. The first adjustment extended member 51 is somewhat triangular shaped and has a rounded triangular shaped aperture 53. Other shapes are possible, but the overall shape here was chosen and designed to enable even and adjustable support pressure to be applied to the leg. The overall triangular shape has the most acute angle of the triangular shape of the first adjustment extended member blending into the upper main support 23, just above the metal plate 31.

Two of the longer sides of the triangular shaped first adjustment extended member 51 extend toward a middle of the upper main support 23 with a lower one of the sides 55 not rising upwardly as sharply as an upper one of the sides 57. As the sides 55 and 57 of the first adjustment extended member 51 continue to diverge, they are attached to a third side 59 which is seen in FIG. 1 as extending somewhat parallel to the elongate length of the brace 21, to complete the triangular shape, and completely surround the rounded triangular shaped aperture 53.

The first adjustment extended member 51 can be curvingly bent farther over and down toward the leg 27, or outward and away from the leg 27. The side 59 can be twisted about the length of the first adjustment extended member 51, or curved concave toward the leg 27 or curved convex toward the leg 27. One advantage of the corner junction between the side 59 and the side 55 is the ability to engage the leg 27 just above the knee to prevent slippage of the brace 21 in the downward direction. The two corners of the first adjustment extended member 51 can be bendably manipulated to engage the leg 27 and derive support from the area above the knee cap, either nearer the center of the leg 27 or farther toward the sides.

A thin contoured pad 61 has an outer edge shape which generally follows, but goes beyond the edges of the upper main support 23, and is seen having a raised area 63 which helps the thin pad 61 remain stationary with respect to the upper main support 23. Note that the thin custom pad 61 has an outer edge 65 which extends just beyond the outer edge of the first adjustment extended member 51, to both protect the leg 27 and enable the bendable engagement with the leg 27 above the knee to prevent slippage.

Adjacent the hinge 41, a second adjustment extended member 71 extends forward and in a direction across the leg 27, but like the first extended member 51 does not extend past the midpoint of the brace 21. In some cases, an additional strap may connect the second adjustment extended member 71 to the first extended member 51. The second adjustment extended member 71 has a slightly different shape, which will become more apparent when viewing the metal plate from which it is formed, in that it has a triangular aperture 73 which has a narrower apex of its most acute angle extending farther into its side of the upper main support 23. Two of the longer sides of the triangular shaped second adjustment extended member 71 extend toward a middle of the upper main support 23 with a lower one of the sides 75 not rising upwardly as sharply as an upper one of the sides 77, the diverging sides 75 and 77 connected to and terminating at a third side 79 which is seen in FIG. 1 as extending somewhat parallel to the elongate length of the brace 21, and spaced apart from and somewhat parallel to third side 59 of the first extended adjustment member 51.

The second adjustment extended member 71 can be curvingly bent in the same manner as the first extended adjustment member 51, and will probably assume a similar overall planar contour as the first adjustment extended member 51. The thin contoured pad 61 has a raised area 81 which extends partially into the triangular aperture 73. Hinge 41 has a polymeric cover 83 which is disposed toward polymeric cover 35.

Examining again the upper main support 23, an opening 85 has a pair of generally straight sides, including a generally horizontal side 87 and generally vertical side 89 with a third curving side 91 completing the triangular enclosure of the opening 85. Behind opening 85 is seen a raised surface of the thin contoured pad 61. Side 89 has a raised section 93 which is partially seen above a strap 95. The raised section 93 is ideally a little wider than the strap 95 and rises away from the leg 27 about the same width as the strap 95. The clearance can be provided by raised section 93 over a portion of the pad 51 having no special structure for strap clearance, or in the alternative, and as will be shown, specific portions of a pad can have depressed clearance structures especially when the metal is not bent into a raised section, such as section 93.

The strap 95 is typically a loop which is doubled at the back side of the brace 21 and which extends through a similar structure on the other side of the upper main support 23, only partially seen in FIG. 1 as an opening 97.

The bendability and thus customizability of the upper main support 23, in addition to the first and second extended adjustment members 51 and 71, is facilitated at the upper corners of the upper main support. Since it is best seen in FIG. 1, the material around opening 85 will be discussed, and it is essentially identical to the corresponding structures around opening 97.

The main extent of the upper main support 23 between the openings 97 and 85 can be bent gently to form over the leg 27. The bending can be done with leather grip pliers or vice grip type pliers, or bending irons or on a mandrel or by hand if the manipulator is strong enough. Once the general shape of the leg is matched, the generally horizontal side 87 provides a lesser width to enable easier bending and customized formation. The lesser width and easier formation is structurally situated in a part of the upper main support 23 which is not designed to undergo great stress, but in which close conformity to the leg 27 will complete the comfort and support conformity which might otherwise be present in a custom brace 21, absent a custom brace's disadvantages.

All of the metal portions of custom brace 21 are preferably covered with a rubber or plastic material which will contribute to wearability, appearance and feel. The rubber or plastic material should be amenable to the use of a tool for adjustment, tolerate the adjustment and yet remain in place as a coating for further wear and or adjustment or it could be bare metal or anodized.

The upper corner at the junction of the generally horizontal side 87 and the generally vertical side 89 can be manipulated to insure that both the generally horizontal side 87 and the generally vertical side 89 fit and lie closely adjacent to the leg 27. The transition from the generally vertical side 89 to the raised section 93 should be generally kept in tact, but in extreme cases it can be adjusted to take account of a thicker or thinner strap 95.

At about the same level as the first and second extended adjustment members 51 and 71, a second strap 99 is seen inserted through a strap aperture 101 just rearward of the first extended adjustment member 51. The strap aperture 101 has a raised portion 103 near the opposite edges of the strap aperture 101 which lifts strap 99 away from the leg 27 to allow easy threading, or insertion of the strap 99. Not seen in FIG. 1 is a similar strap aperture on the other side of the upper main support 23, although this strap aperture is flat, not raised.

Below the hinges 29 and 41, the plates 33 and 45 (plate 45 not seen in FIG. 1) are attached to the lower main support 25. In general, the lower main support 25 has a tighter radius curvature to fit over the shin of the lower leg 27. A third rear strap 107 is seen extending through a strap aperture 109, and like the straps 95 and 99, are doubled to form a loop. The strap aperture 109 is bounded by a portion of the lower main support 25 having a raised portion 111 to enable strap 107 to extend rearwardly around the leg 27 at about the same level as the inner surface of the lower main support 25.

Below the third rear strap 107, a fourth rear strap 113 is seen extending through a lower large aperture 115, a portion of which is left unconformed to the leg 27, for FIG. 1 illustrative purposes. The strap 113, like straps 107, 95 and 99, are doubled to form a loop. A thin contoured pad 117 fits within the lower main support 25, and has a raised area 119 extending through the lower large aperture 115, and which matches the shape of the lower large aperture 115 in order to stabilize the pad 117 with respect to the lower main support 25. To the left of the large opening 115 is a lower large aperture 121. A portion of the thin contoured pad 117 has a raised area 123 extending through the lower large aperture 121, also in order to stabilize the pad 117 with respect to the lower main support 25.

The frontal upper portion of the lower main support 25 has a large, extended "U" shaped main curved opening 125 to enable a significant portion of the front of the leg 27 below the knee to be open to the surrounding air. This main curved opening 125 has a narrower width below its top opening before opening wider as it extends downward.

On either side of the main curved opening 125, is an upper large shaped aperture 127 and an upper large shaped aperture 129, indicated in FIG. 1, but not shown and where a portion of the thin contoured pad 117 has a raised area 131 extending through the large shaped aperture 127. Rather than have an additional strap aperture like strap aperture 109, the strap 107 uses the large shaped aperture 129 to engage the other side of the lower main support 25. The large shaped apertures 127 and 129 define a pair of adjustment members of abbreviated extent as abbreviated adjustment members 133 and 135 opposing each other. Adjustment members 133 and 135 can be adjusted manually or by a manual tool for good fit. Generally, the adjustment members 133 and 135 lift slightly away from the curvature of the lower portion of the leg 27 at sections of the main curved opening 125 which oppose each other at the closest areas of approach. This slight lifting is in order to provide some clearance for a front strap 137. The front strap 137 is also doubled into a loop, similar to the rear straps 95, 99, 107, and 113.

The front strap 137 enables close control of the pressure about the upper shin portion of the lower leg 27 just below the knee. This gives the area of the leg 27 around the main curved opening 125 open non-contacting protection. The open nature of the lower main support 25 enables the strap 137 to control the angle of the right and left sides of the lower main support 25. A tight strap 137 and relatively looser strap 107 puts the right and left sides of the lower main support 25 closer at the front, putting more pressure on the front of the upper shin. A tight strap 107 and a looser strap 137 enables more pressure to be applied to the lower leg 27 on both sides of the shin.

Figure 2:
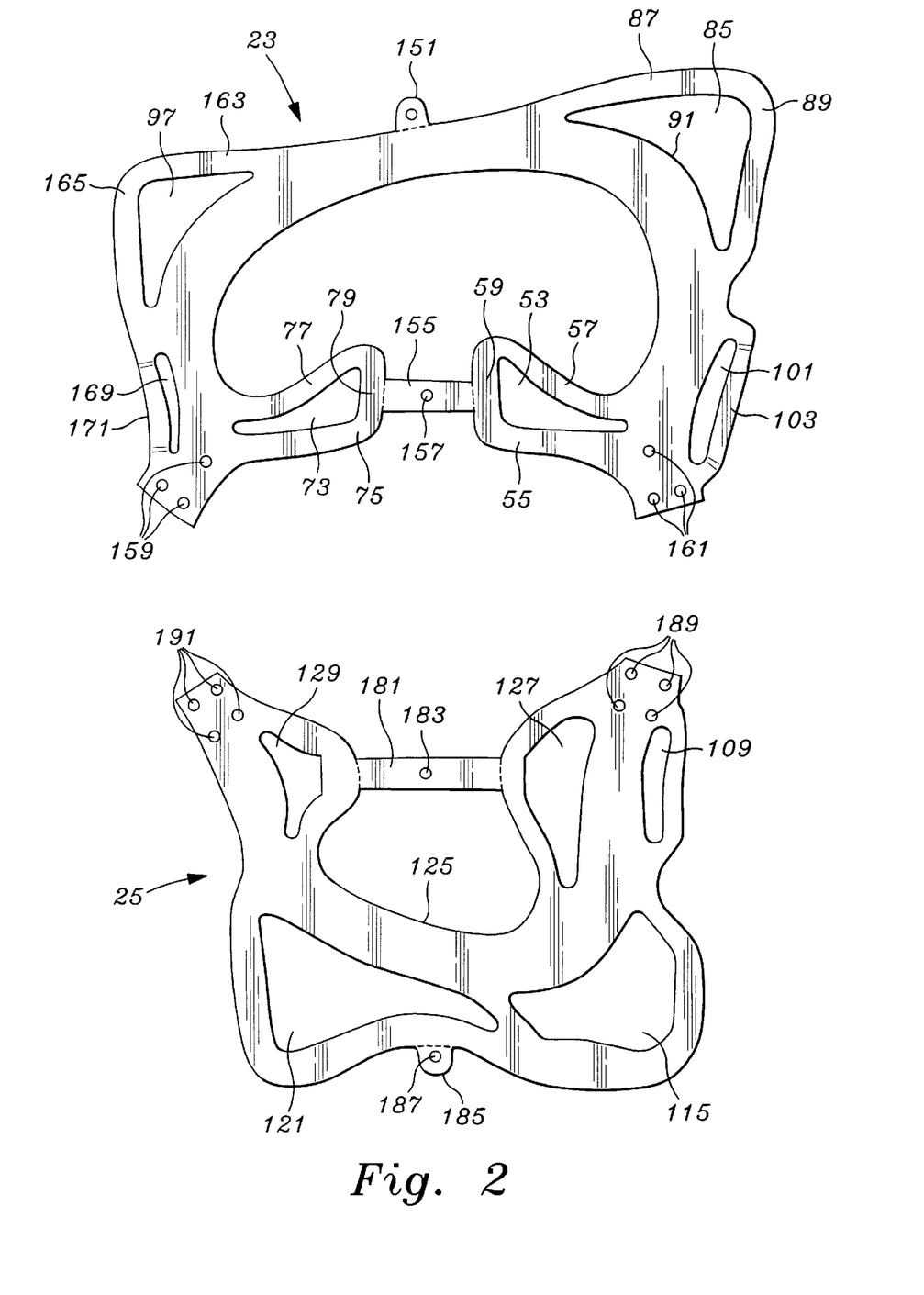
FIG. 2 is a top view of the generally flat metal forms of the upper and lower main support with raised portions to accommodate straps as they would appear after a cutting operation prior to forming and complete with holding webs and tabs used to hold the form during shaping.

Referring to FIG. 2, a view of the upper main support 23 and lower main support 25 is shown in a flat position after just being, cut, stamped, or laser cut out of a sheet of metal, and before formation of the brace 21 seen in FIG. 1. The stamping operation initially leaves an upper holding tab 151 and aperture 153, and middle web 155 and aperture 157. Dashed lines illustrate the location of the cuts which will be made after the material is further processed, for example by adding a chamfer to sets of threaded apertures 159 and 161. An opening 97 has a pair of generally straight sides, including a generally horizontal side 163 and generally vertical side 165. A strap aperture 169 lies adjacent a portion 171.

FIG. 2 illustrates a view of the lower main support 25 is shown in a flat position after just being stamped out of a sheet of metal, and before formation of the brace 21 seen in FIG. 1. The stamping operation initially leaves an upper middle holding web 181 and aperture 183, and a lower tab 185 and holding aperture 187, and may be used to simultaneously form raised portion 111. Dashed lines illustrate the location of the cuts which will be made after the material is further processed, for example by adding a chamfer to sets of threaded apertures 189 and 191.

After the punching of the upper and lower main supports 23 and 25 seen in FIG. 2, the middle holding webs 155 and 181 will remain in place until the upper and lower main supports 23 and 25 are bent about a mandrel having an axis extending generally parallel to a line between the apertures 153 and 187, as seen in FIG. 2, or between the apertures 153 and 157 for upper main support 23, or between apertures 183 and 187 for lower main support 25. After formation of the general semi-cylindrical form seen in FIG. 1, the tabs 151 and 185 are removed along the dashed line indications of FIG. 2, and the holding webs 155 and 157 are removed also along the dashed line indication of FIG. 2. The apertures 159, 161, 189 and 191 may then be threadably tapped to facilitate attachment of the plates 31, 33, 41 and 45 to attach the hinges 29 and 41.

Figure 3:
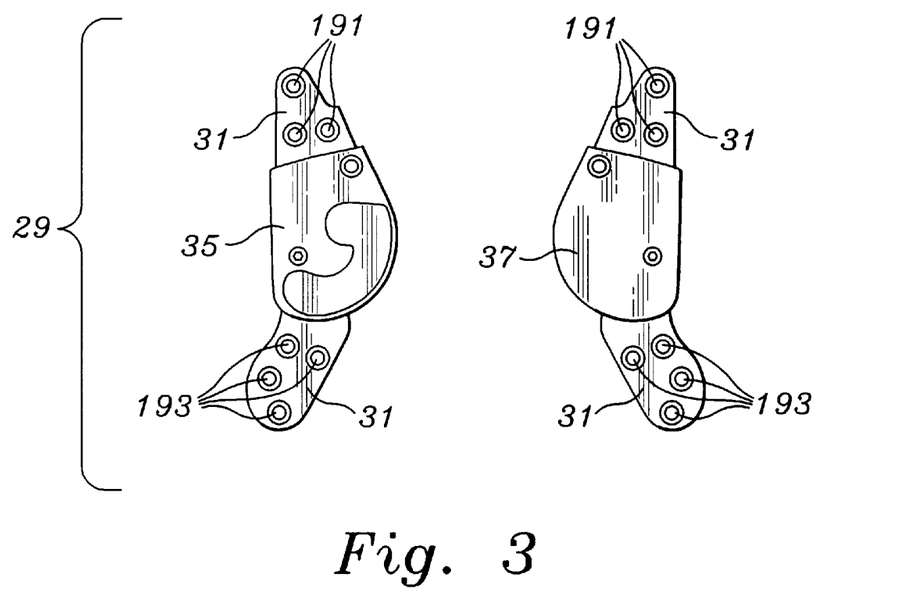
FIG. 3 is an outside and an inside surface view of hinge assembly seen in FIG. 1.

Referring to FIG. 3, the hinge 29 seen in FIG. 1 is seen first at the left in its outward side view and illustrating a series of three chamfered screw apertures 191 on plate 31 and a series of four chamfered screw apertures 193. At the right, the inward side view of the hinge 29 is seen.

Figure 4:
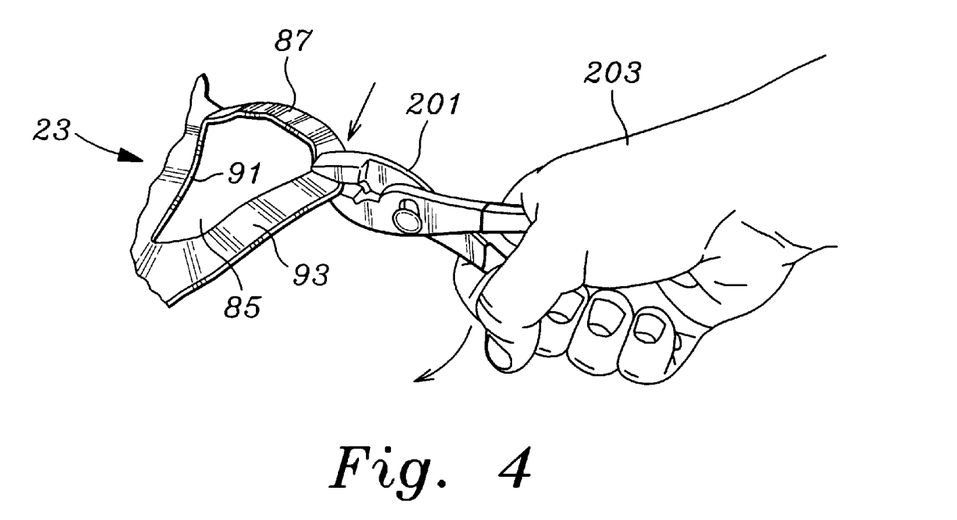
FIG. 4 illustrates the adjustment, manually with a pliers tool for facilitating bending which can be done at the corners of the upper and lower main support, at the extended adjustment members, and at the abbreviated adjustment members.

Referring to FIG. 4, the upper corner of the upper main support 23, including horizontal side 87 and vertical side 93, as well as third curving side 91 is shown. A pair of pliers 201 can be manipulated by a user 203 to adjust horizontal side 87 and vertical side 93, and third curving side 91.

Figure 5:
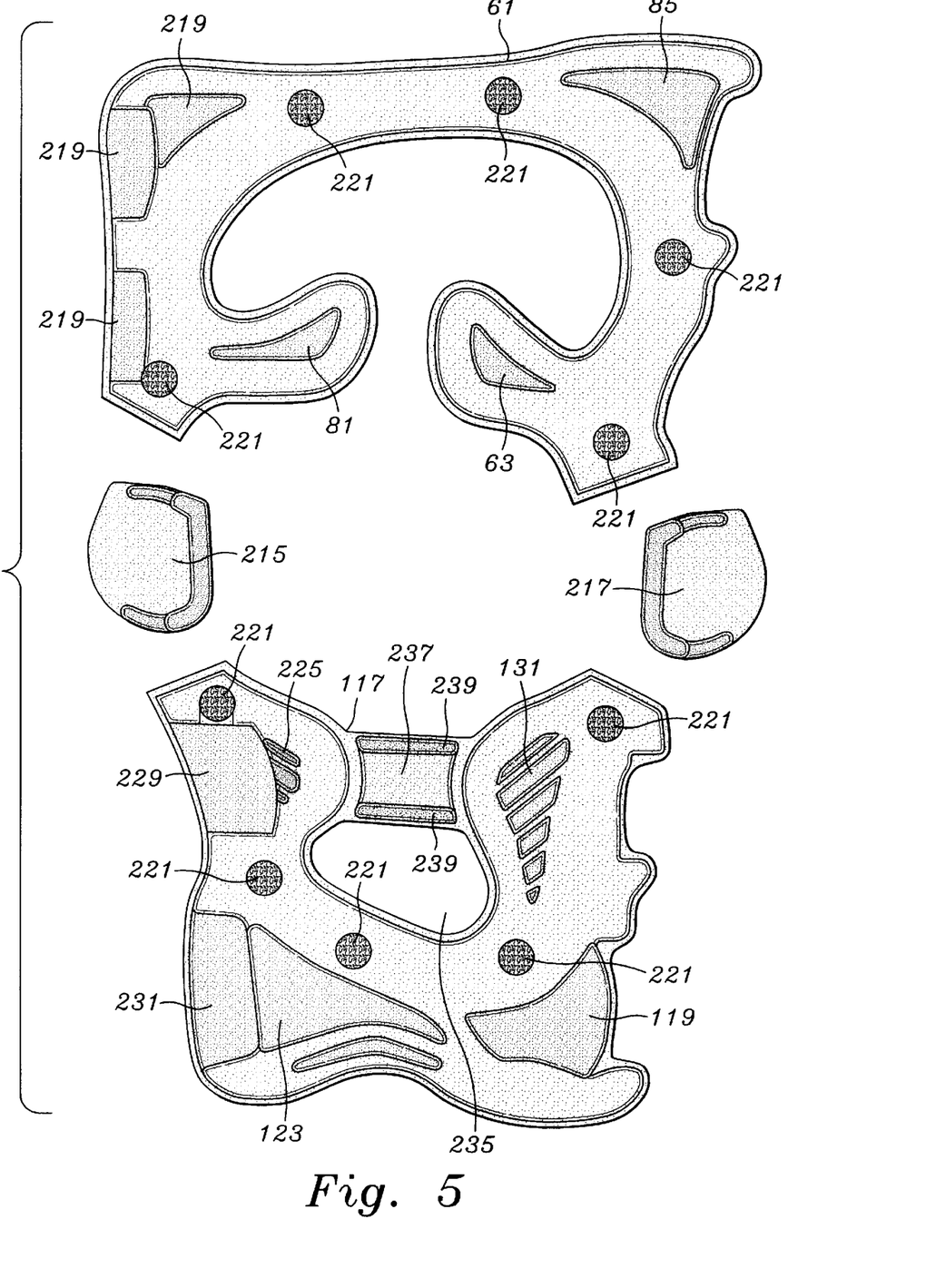
FIG. 5 illustrates a thin contour pad set for fittable and perhaps removable attachment to the upper and lower main supports, and inside and outside hinges to give additional comfort to the user.

Referring to FIG. 5, an expanded and flattened view of the thin contoured pads 61 and 117 as well as a pair of hinge pads 215 and 217. At the upper left of the pad 61 is seen a raised area 218 not previously seen in FIG. 1, as well as the raised areas 63, 81 and 85 previously seen. A series of patches of material 221 which may be one of hook material and loop material are distributed about the pad 61 for engagement with the other of hook material and loop material attached to the back or inside of the brace 21 to be held into place. Also seen at the left side of the pad 61 are a pair of depressions 219 and to facilitate the passage of the straps 95 and 99, respectively without creating a lump or inner bulge against the leg 27.

The hinge pads 215 and 217 may also have hook and loop material, but given that they may be spaced apart from the leg 27, they may be glued or adhesive fastened to the polymeric cover 83 on the inside opposing faces of the brace 21, or attached with hook and loop members.

The thin contoured pad 117 is shown in flat folded out position and is also seen as having a series of patches of material 221. The raised areas 119, 123, and 131 are shown, as well as a raised area 225 which was not seen in FIG. 1. A pair of depressions 229 and 231 are seen at the left side of the pad 117 to facilitate the passage of the straps 107 and 113, respectively without creating a lump or inner bulge against the leg 27.

An aperture 235 is seen in the pad 117 since the upper portion of the "U" shaped opening of the lower main support 25 is expected to be covered by front strap 137. A pad web 237 includes a pair of spaced apart guide ribs 239 to help stabilize front strap 137 as it extends between apertures 127 and 129.

Figures 6, 7:
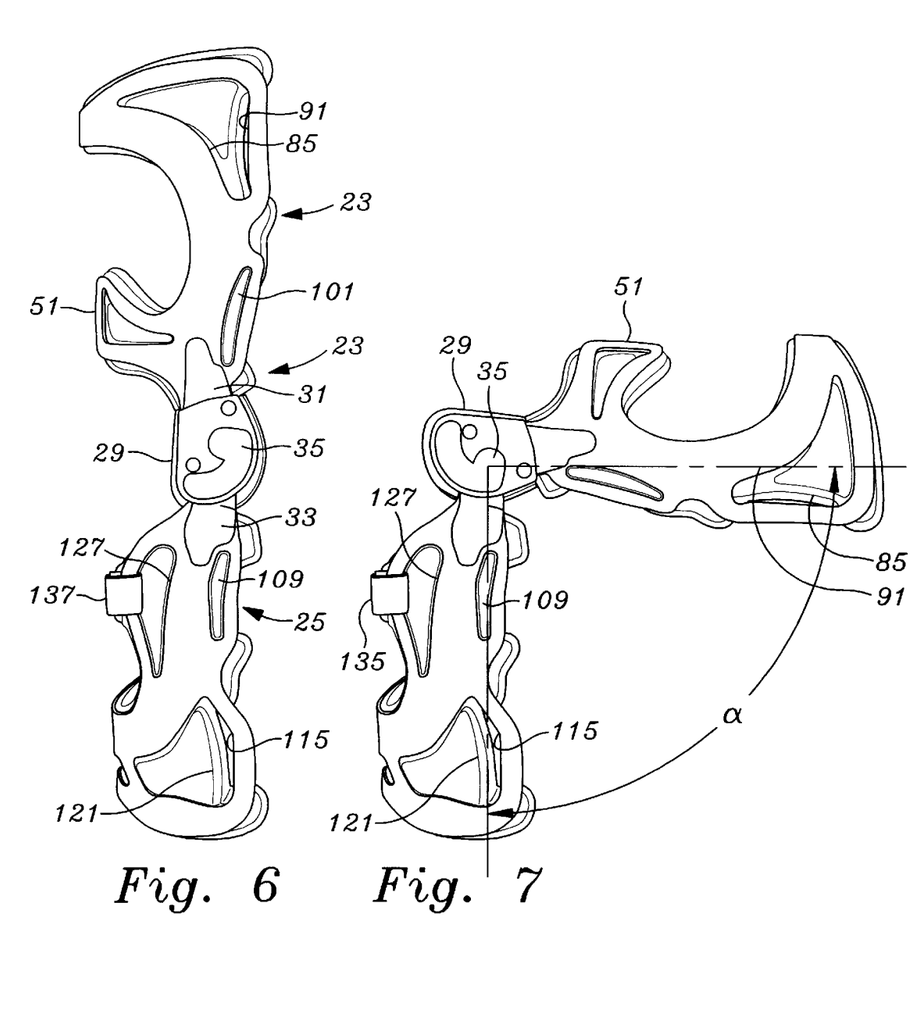
FIG. 6 is a side view of the brace of FIG. 1, and without the rear straps and illustrating a fully extended position.
FIG. 7 is a side view of the brace as seen in FIG. 6 and illustrating an angular displacement.

Referring to FIG. 6, a side view of the brace 21 seen in FIG. 1 more clearly illustrates the alignment of the openings 85 and 97, 53 and 81, & 115 and 121. FIG. 7 illustrates the angular movement of the upper main support 23 with respect to the lower main support 25 and moving about an angle α.

Figure 8:
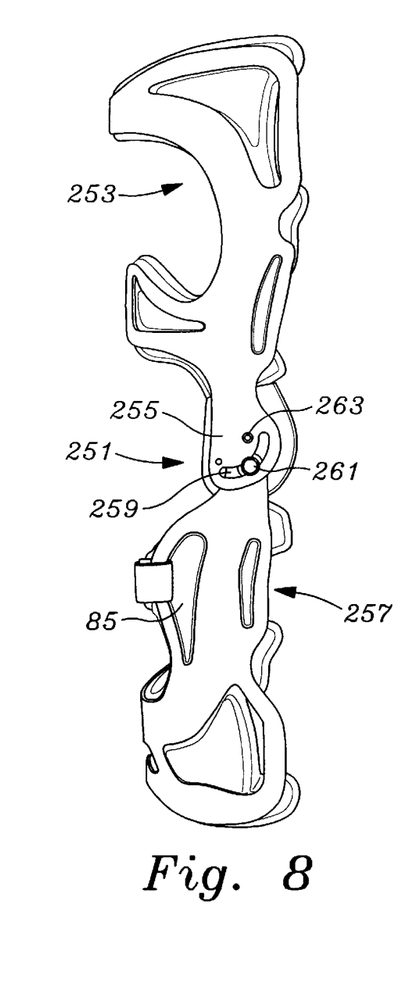
FIG. 8 is an alternative brace in which the hinge is formed integrally with the upper and lower main supports.

Referring to FIG. 8, a brace 251 has an upper main support 253 having an integrally formed hinge member 255, and a lower main support 257 having an integrally formed hinge member 259 which is partially shown behind the hinge member 255. The hinge members 255 and 259 interfit with each other and enable angular bending of the support 253 with respect to the support 257. A pair of pins 261 and 263 are displaced in slots, such as slot 265 seen in FIG. 8 to control the relationship of the upper and lower main supports 253 and 257 as they are angularly displaced with respect to each other.

While the present invention has been described in terms of a leg brace, one skilled in the art will realize that the structure and techniques of the present invention can be applied to many similar structures. The present invention may be applied in any situation where extending distribution of bending moment is desired, where adjustability of shape is desired, but without having to also provide a constraining confining solid area coverage.

Although the invention has been derived with reference to particular illustrative embodiments thereof, many changes and modifications of the invention may become apparent to those skilled in the art without departing from the spirit and scope of the invention. Therefore, included within the patent warranted hereon are all such changes and modifications as may reasonably and properly be included within the scope of this contribution to the art.

What is claimed:

1. An adjustable knee brace adjustable bendable by a user to a stable shape comprising:

an upper main support having an upper main support first side having a first length having a first lower end, an upper main support second side having a second length having a second lower end, and a forward curving upper transition between said first and second lengths, a first extended adjustment member continually adjustable extending from said first length near said first lower end, a second extended adjustment member extending from said second length near said second lower end, said first and second extended adjustment members extending curvingly toward each other in a spaced apart relationship;

a lower main support having a lower main support first side having a first upper end, and extending downwardly and forwardly across to a lower main support second side and extending upward to a second upper end;

a first hinge attached between said first lower end and first in its place upper end; and a second hinge attached between said second lower end and said second upper end, to form said knee brace and to facilitate and control the angular displacement of said lower main support rearwardly with respect to said upper main support.

2. An adjustable knee brace comprising:

an upper main support having an upper main support first side having a first length having a first lower end, an upper main support second side having a second length having a second lower end, and a forward curving upper transition between said first and second lengths, a first extended adjustment member extending from said first length near said first lower end, a second extended adjustment member extending from said second length near said second lower end, said first and second extended adjustment members extending curvingly toward each other;

a lower main support having a lower main support first side having a first upper end, and extending downwardly and forwardly across to a lower main support second side and extending upward to a second upper end;

a first hinge attached between said first lower end and first upper end; and a second hinge attached between said second lower end and said second upper end, to form said knee brace and to facilitate and control the angular displacement of said lower main support rearwardly with respect to said upper main support, and wherein said first extended adjustment member further comprises a first triangular loop extending from said first length near said first lower end and wherein said second extended adjustment member further comprises a second triangular loop extending from said second length near said second lower end.

3. The adjustable knee brace as recited in claim 1 wherein said first extended adjustment member further comprises a first triangular loop having a first and second side each having first ends integral with said first length near said first lower end and extending from said first length and each having a second end, and a third side having a first end connected to said second end of said first side of said first triangular loop, and a second end connected to said second end of said second side of said first triangular loop, and wherein said second extended adjustment member further comprises a second triangular loop having a first and second side having first ends integral with said second length near said second lower end and extending from said second length and each having a second end, and a third side having a first end connected to said second end of said first side of said second triangular loop, and a second end connected to said second end of said second side of said second triangular loop.

4. The adjustable knee brace as recited in claim 1 wherein said upper main support has an upper top edge and a first outer side edge and a first upper corner having a first opening having an upper edge which forms a first upper side with said upper top edge, and having a side edge which forms a second upper side with said first outer side edge, and having a first connecting edge extending between said upper edge and said side edge, and wherein said first upper side and said second upper side may be adjustably bent to closely conform said upper main support adjacent said first corner to a user's upper leg, said first upper side and said second upper side forming a first edge adjustment zone.

5. The adjustable knee brace as recited in claim 4 wherein said upper main support has a second outer side edge and second upper corner having a second opening having an upper edge which forms a third upper side with said upper top edge, and having a side edge which forms a fourth upper side with said second outer side edge, and having a second connecting edge extending between said upper edge and said side edge, and wherein said third upper side and said fourth upper side may be adjustably bent to closely conform said upper main support adjacent said second corner to a user's upper leg, said third upper side and said fourth upper side forming a second edge adjustment zone.

6. The adjustable knee brace as recited in claim 1 wherein said first hinge has a first member integral with said first lower end and a second member integral with said first upper end, and wherein said second hinge has a first member integral with said second lower end and a second member integral with said second upper end.

7. The adjustable knee brace as recited in claim 4 wherein said first connecting edge is curved convex within said first opening of said first upper corner and can be bendably adjusted to form a first additional adjustment zone.

8. The adjustable knee brace as recited in claim 5 wherein said first and second connecting edges are curved convex within their respective said first and second openings of said first and second upper corner and can be bendably adjusted to form a first and a second additional adjustment zones.

9. The adjustable knee brace as recited in claim 5 wherein said second upper side of said first opening and said fourth upper side of said second opening have a raised section for accommodating engagement by a rear strap by giving additional clearance between said upper main support and a user's leg.

10. The adjustable knee brace as recited in claim 6 and further comprising a first thin contoured pad following a general shape of said upper main support and having at least two raised areas, including a first raised area associated with said first opening of said first corner and a second raised area associated with said second opening of said second corner.

11. The adjustable knee brace as recited in claim 2 and further comprising a first thin contoured pad following a general shape of said upper main support and having at least two raised areas, including a first raised area associated with and extending at least partially through said first triangular loop of said first extended adjustment member and a second raised area associated with and extending at least partially through said second triangular loop of said second extended adjustment member to assist in stabilizing said first thin contoured pad with respect to said upper main support.

12. The adjustable knee brace as recited in claim 1 wherein said lower main support has a first upper shaped aperture forward of said first upper end and a second upper shaped aperture forward of said second upper end and wherein said lower main support has a main curved opening, said first upper shaped aperture and said main opening having a first adjustment member therebetween, and said second upper shaped aperture and said main opening having a second adjustment member therebetween.

13. The adjustable knee brace as recited in claim 1 wherein said lower main support has a lower edge and a first lower shaped aperture adjacent said lower edge of said lower main support and a second lower shaped aperture adjacent said lower edge of said lower main support, said first and said second lower shaped apertures facilitating engagement of a rear strap for holding said lower main support in place with respect to a user.

14. The adjustable knee brace as recited in claim 13 wherein said lower main support has a first side edge and a second side edge and wherein said first lower shape aperture and said lower edge of said lower main support and said first side edge of said lower main support have a first lower adjustment zone therebetween, and wherein said second lower shape aperture and said lower edge of said lower main support and said second side edge of said lower main support have a second lower adjustment zone therebetween.

15. The adjustable knee brace as recited in claim 13 and further comprising a first thin contoured pad following a general shape of said lower main support and having at least two raised areas, including a first raised area associated with and extending at least partially through said first lower shaped aperture of said lower main support and a second raised area associated with and extending at least partially through said second lower shaped aperture of said lower main support to assist in stabilizing said first thin contoured pad with respect to said lower main support.

16. An adjustable knee brace comprising:

an upper main support having an upper first side having a first uppermost extent and a first lowermost extent, and an upper second side having a second uppermost extent and a first lowermost extent, said first side of said upper main support and said second side of said upper main support connected by a structural extension therebetween, at least a first extended bendable adjustment member extending from said upper first side and toward said upper second side short of said upper second side for providing adjustable support of said adjustable knee brace against a leg of a user;

a lower main support having a lower main support first side having a first upper extent, a lower main support second side and extending upward to a second upper extent, said lower main support second side connected to said lower main support first side;

a first hinge attached between said first lowermost extent and said first upper extent; and a second hinge attached between said second lowermost extent and said second upper extent, to form said knee brace and to facilitate and control the angular displacement of said lower main support rearwardly with respect to said upper main support.

17. The adjustable knee brace as recited in claim 16 wherein said at least a first extended bendable adjustment member further comprises a first triangular loop.

18. The adjustable knee brace as recited in claim 17 and further comprising at least a second extended bendable adjustment member extending from said upper second side and toward said upper first side short of said upper first side for providing adjustable support of said adjustable knee brace against a leg of a user.

19. An adjustable knee brace comprising:

an upper main support having an upper first side having a first uppermost extent and a first lowermost extent, and an upper second side having a second uppermost extent and a second lowermost extent, said first side of said upper main support and said second side of said upper main support connected by a structural extension therebetween;

a lower main support having a lower main support first side having a first upper extent, a lower main support first side and extending upward to a second upper extent, said lower main support second side connected to said lower main support first side, at least a first extended bendable adjustment member extending from said lower main support first side and toward said lower main support second side short of said lower main support second side for providing adjustable support of said adjustable knee brace against a leg of a user;

a first hinge attached between said first lowermost extent and said second upper extent; and a second hinge attached between said second lowermost extent and said second upper extent, to form said knee brace and to facilitate and control the angular displacement of said lower main support rearwardly with respect to said upper main support.

20. The adjustable knee brace as recited in claim 19 and further comprising at least a second extended bendable adjustment member extending from said lower main support second side and toward said lower main support first side short of said lower main support first side for providing adjustable support of said adjustable knee brace against a leg of a user.

* * * * *